United States Patent [19]

Arbogast et al.

[11] Patent Number: 4,865,612
[45] Date of Patent: Sep. 12, 1989

[54] PROSTHETIC FOOT

[75] Inventors: Robert E. Arbogast; C. Joseph Arbogast, both of Mt. Sterling, Ohio

[73] Assignee: The Ohio Willow Wood Company, Inc., Mount Sterling, Ohio

[21] Appl. No.: 122,542

[22] Filed: Nov. 12, 1987

Related U.S. Application Data

[63] Continuation of Ser. No. 889,885, Jul. 28, 1986, abandoned.

[51] Int. Cl.$^4$ .............................................. A61F 2/66
[52] U.S. Cl. ....................................................... 623/55
[58] Field of Search ..................................... 623/53–56

[56] References Cited

U.S. PATENT DOCUMENTS

| | | |
|---|---|---|
| 61,780 | 2/1867 | Watson . |
| 464,356 | 12/1891 | Gault . |
| 496,645 | 5/1893 | Gault . |
| 546,405 | 9/1895 | Marks . |
| 563,247 | 7/1896 | Andrews . |
| 616,873 | 1/1899 | Andrews . |
| 1,289,580 | 12/1918 | Vincenti . |
| 1,420,330 | 6/1922 | Marks . |
| 1,617,926 | 2/1927 | Shrodes . |
| 2,289,154 | 7/1942 | Van Cise ................................... 3/6 |
| 2,475,372 | 7/1948 | Catranis ..................................... 3/6 |
| 3,484,871 | 12/1969 | Orange ................................... 623/55 |
| 3,766,569 | 10/1973 | Orange ....................................... 3/7 |
| 3,784,988 | 1/1974 | Trumpler ................................. 3/18 |
| 3,920,610 | 11/1975 | Wagner ................................. 623/55 |
| 4,177,525 | 12/1979 | Arbogast et al. ........................... 3/7 |
| 4,547,913 | 10/1985 | Phillips ................................. 623/27 |
| 4,645,509 | 2/1987 | Poggi ................................... 623/55 |

FOREIGN PATENT DOCUMENTS

| | | |
|---|---|---|
| 361972 | 1/1923 | Fed. Rep. of Germany . |
| 2341887 | 2/1975 | Fed. Rep. of Germany . |
| 778732 | 3/1977 | U.S.S.R. . |
| 6968610 | 6/1978 | U.S.S.R. . |
| 5356 | 3/1913 | United Kingdom . |
| 1420627 | 1/1976 | United Kingdom . |

OTHER PUBLICATIONS

Brochure entitled "The Seattle Foot".
Brochure entitled "The Seattle Foot—Alignment and Installation Manual".

Primary Examiner—Richard J. Apley
Assistant Examiner—James Prizant
Attorney, Agent, or Firm—Ronald P. Kananen

[57] ABSTRACT

An artificial foot includes a hollow, rigid, compression-molded composite keel made from aramid fiber-reinforced plastic for connection to a prothesis and to an improved composite carbon-fiber material acting as a spring for improving the energy absorbing and releasing characteristics of the foot to aid movement of the amputee. The spring includes a pair of thin, forwardly-extending composite spring members capable of lateral movement with respect to each other and connected to the keel. An auxiliary deflection spring or plate is interposed between the primary deflection plate and the keel and includes a forwardly-extending upwardly-oriented portion to aid in energy absorption and release during flexing of the foot. The plates are surrounded by a suitable abrasion resistant material, such as a Kevlar sock, surrounded by a low density flexible foam urethane. A medium density flexible foam urethane wedge is interposed beneath the heel portion of the keel. The composite construction is surrounded by an outer shell formed in the shape cosmetically to resemble a foot. The keel structure and method of making the composite to provide longitudinal and transverse strength are also disclosed.

33 Claims, 3 Drawing Sheets

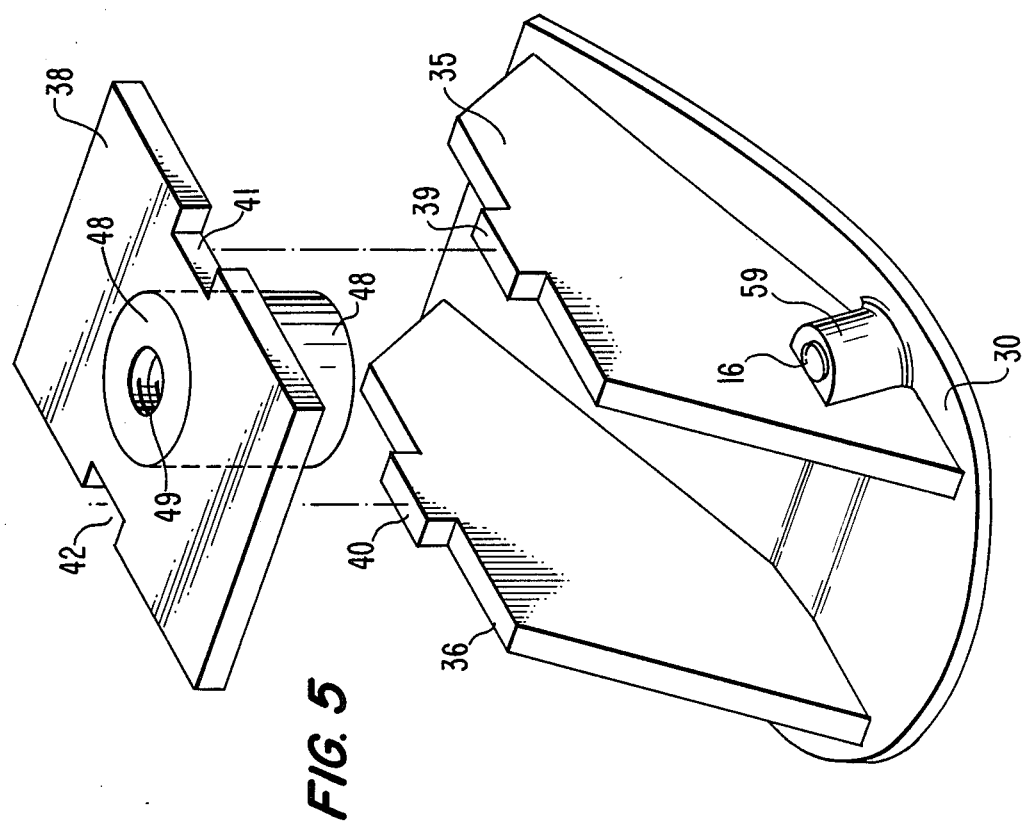
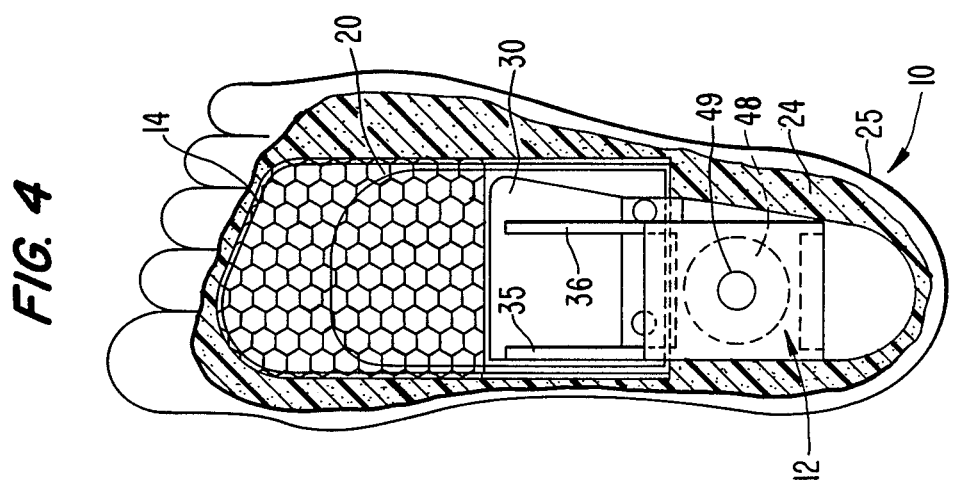

PROSTHETIC FOOT

This application is a continuation of application Ser. No. 889,885, filed 7/28/86, now abandoned.

BACKGROUND OF THE INVENTION

This invention relates to an artificial or prosthetic foot. More particularly, this invention relates to a prosthetic foot which incorporates improved energy storing capabilities by using an auxiliary deflection plate. Still more particularly, this invention relates to a lightweight prosthetic foot which, with its energy storage capabilities, provides a smooth natural motion for the user. Still more particularly, this invention relates to a prosthetic foot having an improved keel, spring structure, and method of manufacture which provides a lightweight, easy-to-use, yet sturdy S.A.C.H. prosthetic foot.

A number of types of prosthetic feet are known to the art which attend to various problems relating to the structure, cosmetic appearance, weight, and energy storage and transfer characteristics of the foot. An early design of a prosthetic foot incorporated a leather hinge across the ball of the foot with natural rubber positioned in a v-groove above the hinge. In use, the rubber member was compressed to store energy for the next step of the user. Later examples of such feet utilized various elastic materials acting as springs and energy absorbers. Thus, the notion that energy storage capabilities within a prosthetic foot could be advantageous to an amputee is not new. Such a device today is unsatisfactory because of its weight at the furthest point from the knee center which creates a large moment resulting in high stresses about the knee and greater impact at full extension of the leg. Moreover, such a device does not provide the amputee with sufficient energy storage capabilities and is unacceptable cosmetically.

Another prosthetic foot introduced about 1960 included an inner keel of wood surrounded by flexible foam plastic. The plastic has a sufficient density to permit limited resistance to bending, thus creating some energy storing characteristics. Later devices have improved upon this design by carving keels from solid, homogeneous plastic blocks in an effort to relieve some of the stresses on the flexible foam plastic and to allow somewhat greater energy storage characteristics. However, these solutions have not proven to be completely satisfactory because of the weight of the foot and the eventual failure of the flexible foam urethane. In U.S. Pat. No. 4,177,525 an artificial foot construction is shown as having a rigid keel made from a molded plastic material with a metal reinforcing strip embedded within the plastic keel portion near the lower surface. The keel is surrounded by a typical flexible foam plastic material molded to the keel to form the outer surface of the foot. While this device has proven to be commercially acceptable, it remained a problem in the art to improve upon that artificial foot by incorporating significantly improved energy storing capabilities, and selecting materials which made the device lightweight, yet sturdy, and capable of a long commercial life.

In U.S. Pat. Nos. 3,484,871 and 3,766,569 the concept of utilizing leaf springs in an artificial foot is shown. An artificial foot having a solid inelastic core preferably made of wood extends substantially the entire height of the foot. A front core portion extends forwardly of the main core to receive an upwardly-offset, flat, spring seat for receiving a flat, elastic leaf spring made from a pair of spring plates of uniform gauge, width, and length, and arranged in a laminar form. A flexible plastic liner, preferably made of Teflon brand material, is interposed between the plates. The strength and gauge of the spring plates is such that when the foot is flexed, such as when the weight of the wearer shifts forward over the ball of the foot in walking, the spring will flex about the ball of the foot and maintain its elastic properties to restore the toe of the foot to its original position after each walking step when the weight of the wearer is released. A protective webbing material, such as a Nylon brand material, is fitted between the lower spring plate and the sole to reduce wear, while the foot is surrounded by a resilient cover.

Thus, it is an aim in this art to provide a lightweight prosthetic S.A.C.H. artificial foot made from materials and constructed to exhibit favorable walking and running characteristics. To this end, attention is particularly given in this invention to an improved keel construction, the keel material, an improved spring construction, the spring material, and to a method of making the spring.

Notwithstanding those feet in the art, it has remained a particular problem to improve upon the energy transfer characteristics of the foot. Thus, is an overall objective of this invention to utilize an improved spring structure made from a composite material and having sufficient energy storing capability to meet the needs of the user.

It is another overall object of this invention to provide a lightweight prosthetic foot of the type described having a strong, yet lightweight, rigid compression molded composite keel.

It is still another object of this invention to provide a prosthetic foot of the type described which utilizes a laminate of a fiber-reinforced, carbon composite for the spring plates.

It is still another object of this invention to provide a prosthetic foot having a primary carbon-composite deflection plate and an auxiliary carbon-composite deflection plate for improving the energy storage and release characteristics of the foot, while ensuring its light weight.

These and other objects of the invention will become apparent from the detailed written description of the invention which follows, taken in conjunction with the accompanying drawings.

BRIEF SUMMARY OF THE INVENTION

Directed to achieving the foregoing objects and overcoming the problems in the prior art, while improving the energy storage and release capabilities of an artificial foot with a lightweight construction, the artificial foot according to one aspect of the invention comprises a lightweight, yet rigid compression-molded composite keel. The keel is manufactured from an aramid fiber-reinforced, Nylon brand, thermoplastic having high impact resistance, and little compression set, while being resistant to fracture. The keel is made from a bottom plate and a pair of opposed, upwardly-extending side walls forming hollow forwardly- and rearwardly-opened channels, for receiving a lightweight material therein, and closed at its top by an upper plate secured to the side walls.

A primary deflection plate is made from a thermoset carbon, fiber-reinforced, multiple-layer, laminate secured to a lower, forward portion of the keel. An auxiliary deflection plate is interposed between the primary deflection plate and the keel and includes a forward, upwardly-curved portion at about the area of flexure of the foot. The graphite or carbon composite material provides significantly improved energy storage and release capability over metallic springs. Preferably, the carbon, flat spring is produced with fibers oriented relatively longitudinally and transversely so that the short, forwardly extending flat spring may undergo a large amount of deflection while resisting stresses. The method of manufacture of the deflection plate by longitudinally and transversely orienting the fibers is also a significant feature of this invention.

Alternatively, the auxiliary spring member may be made from a plastic material secured to the keel, or integrally formed with and of the same material as the keel.

The spring structure is preferably surrounded with a protective sock, preferably made of a Kevlar brand material, about which a low-density, flexible thermoplastic material, such as foam urethane is molded to provide an attractive appearance for the foot. A medium density flexible foam urethane wedge is disposed beneath the heel portion of the foot.

These and other features of the invention will also become apparent from a detailed written description which follows.

BRIEF SUMMARY OF THE DRAWINGS

In the drawings:

FIG. 4 is another top plan view similar to FIGS. 2 and 3 showing a protective sock surrounding the deflection plates;

FIG. 5 is an exploded perspective view of the keel structure according to the invention;

DETAILED DESCRIPTION OF THE PREFERRED EMBODIMENT

Figure 1:
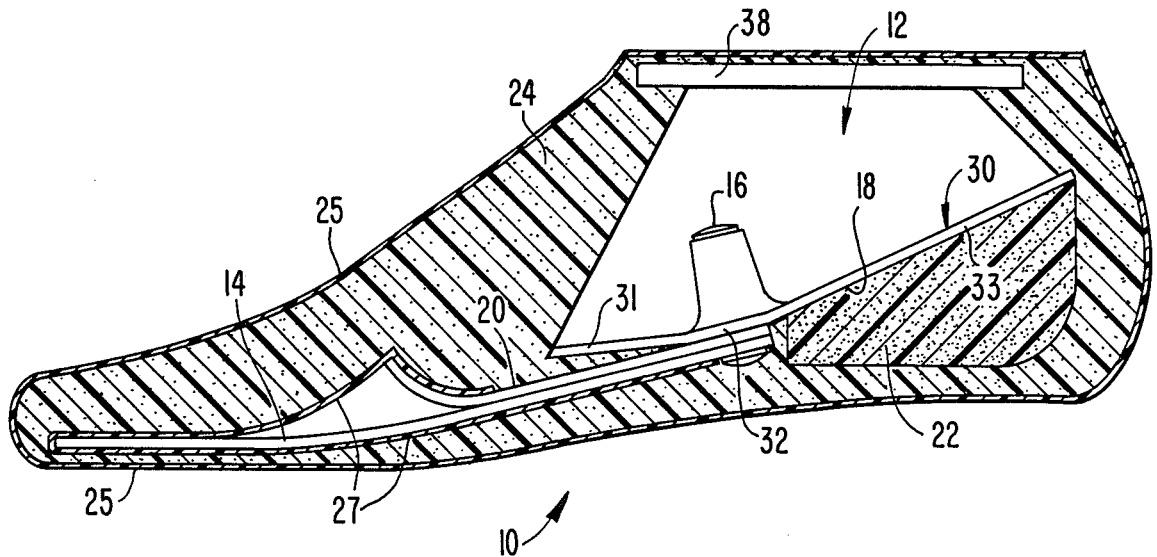
FIG. 1 is a side cross-sectional view showing the components of the improved prosthetic foot according to the invention.
Figure 2:
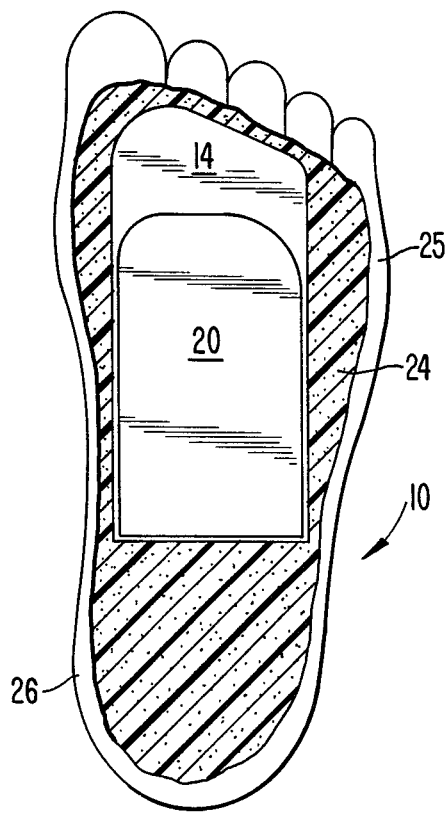
FIG. 2 is a top plan portion of the foot of FIG. 1 taken along a lower portion thereof and showing the primary and auxiliary deflection plates.
Figure 3:
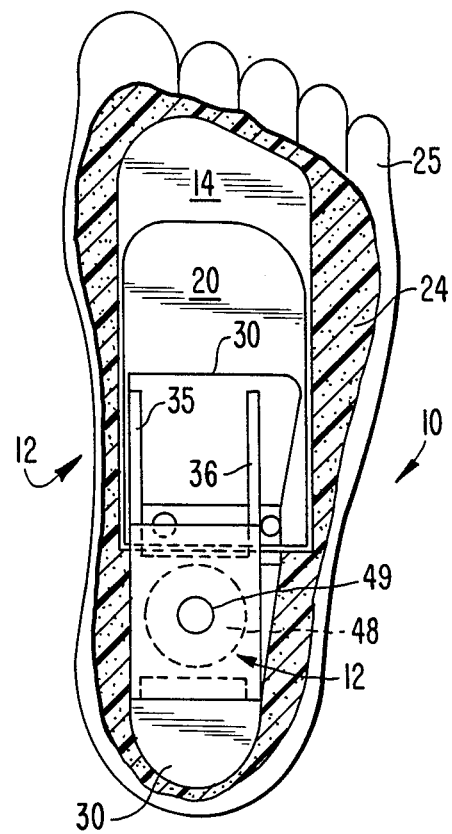
FIG. 3 is a view similar to FIG. 2 showing a top view of the keel secured to the deflection plates.

In FIGS. 1-4, a prosthetic foot according to the invention is designated generally by the reference numeral 10. The foot 10 includes a rigid, compression-molded composite keel 12 to which is secured a primary carbon deflection plate 14 by fastening member 16 to a lowermost surface 18 of a lower wall of the keel 12. An auxiliary composite deflection plate 20 is similarly secured to the surface 18 of the keel 12, intermediate the primary deflection plate 14 and the lowermost surface 18 of the keel 12. A medium-density, flexible, foam-urethane wedge 22 is located beneath the lower surface 18 of the keel 12, rearward of the fastener 16. A low density flexible foam urethane member 24 is provided about the keel and spring structure and is further surrounded by an aesthetically-appearing, cosmetically-true plastic covering 25 resembling a foot.

The keel 12 includes a laterally-extending lower wall 30 defining the lower surface 18 and having a forwardly-extending portion 31, an intermediate, upwardly-extending portion 32, and an rearwardly-extending portion 33. The angle of inclination in the rearward direction of the portion 32 is intermediate that of the forwardly-extending portion 31 and that of the rearwardly-extending portion 33.

The keel 12 further includes a pair of opposed vertically-extending walls 35, 36 spaced apart and defining a hollow channel open at its front and rear to define, a receptable for receiving a light-weight foam material therein. The walls 35, 36 are joined at their uppermost top surfaces 35a, 36a by a top plate 38 having an opening 49 therein for receiving a connection to an artificial limb structure. Thus, the walls 35 and 36 when molded provided a unitary construction with the bottom plate 30 to define a box-shaped receptacle having an irregular shape which is closed by the top plate 38. Preferably the top member 38 has a pair of opposed, spaced recesses 41, 42 at its opposed edges for mating with upwardly-extending projections 39, 40 on an uppermost surface of the side walls 35, 36.

A pair of opposed, bosses 59 are molded outwardly of the side walls 35, 36 for receiving the fasteners 16 in a secure, sturdy relationship. The top plate 38 preferably includes a downwardly-extending boss 48 having a metallic insert 49 for receiving a threaded member of the prosthesis.

Preferably, the keel 12 is manufactured from an aramid, fiber-reinforced Nylon thermoplastic. These materials typically demonstrate extreme impact resistance, little compression set, and are sufficiently lightweight to reduce significantly the weight of the foot. By using this material for the keel 12, and in the hollow construction described, the keel is lightweight creating a smaller moment about the axis of the knee and thus causes significantly less impact at full extension of the prosthesis during walking or running. The structural design renders the keel 12 highly resistant to fracture, in comparison to prosthetic feet with wooden keels. The thermoplastic material also exhibits a very low compression set and water absorption characteristics, assisting in eliminating a problem of the foot becoming loose from the remaining artificial limb or prosthesis at its attachment point as is common with keels manufactured from both wood and homogeneous plastics.

Figure 6:
FIG. 6 is a side view of the laminated spring plate construction.

As best seen in FIG. 6 the primary deflection plate 14 is made from a pair of thin fiber-reinforced, carbon deflection plates 14a, 14b; which are slidable relative to each other about the fastener 16. The use of a thermoset carbon-reinforced multiple-spring 14 attached to the keel 12 provides significant advantages. Foremost, this material replaces the mechanical function of both a flexible, foam, plastic shell and other materials to share some of the other required load-bearing characteristics compared to some prosthetic feet known to the art. Such a design provides significant energy storage characteristics in comparison with other designs, but with a lightweight material and small required volume, permitting the grouping of the plates to be fashioned in a design that allows the amputee to more closely demonstrate the gait of a normal person.

The strength of the structure when made from a graphite or carbon composite material exhibits significant advantages over conventional heat-treated steel. From a beam analogy, a beam can be considered to be composed of an infinite number of small diameter fibers running from end to end. A beam thus supported at each end will measurably deflect when a weight is applied to the middle of the beam to cause the beam to bow downwardly. The fibers on the outermost surface of the beam, i.e., the top and bottom flanges of the beam, undergo the greatest amount of stress because their compression at the top is at a maximum while the fibers on the lowermost or bottom surface of the beam will undergo the maximum tensile forces. Thus, the fibers on the lowermost portion of the bottom flange of the beam are subjected to the greatest amount of tensile load so that the strength of these fibers determines the ultimate strength of the beam. The tensile strength of graphite composite fibers is about 250,000 psi. while the tensile strength of steel is about 80,000 psi. This differential means that the beam can be loaded with nearly three times the load of a steel beam before permanent deformation or fracture. In addition, the graphite composite has a significantly less weight per volume compared to steel. The density of the graphite composite is about 0.058 lbs./cu. inch as opposed to 0.282 lbs./cu. inch for steel. Thus, the weight per unit volume of the graphite composite is only about 20% that of steel. Accordingly, a graphite beam will be about 15 times as resistant to deflection compared to a steel beam using the same material weights or, conversely, a graphite beam having the same resistance as a steel beam will only weigh about 1/15 as much as the steel beam. Moreover, the modulus of elasticity of the graphite composite is approximately that of the steel.

The spring is made up, as described, from a plurality of layers of unidirectional pre-preg graphite material which is commercially available with an epoxy and a removable backing. The composite is cured as is known in the art. Strips of such material are successively laminated with the fiber direction oriented as described.

Figure 7:
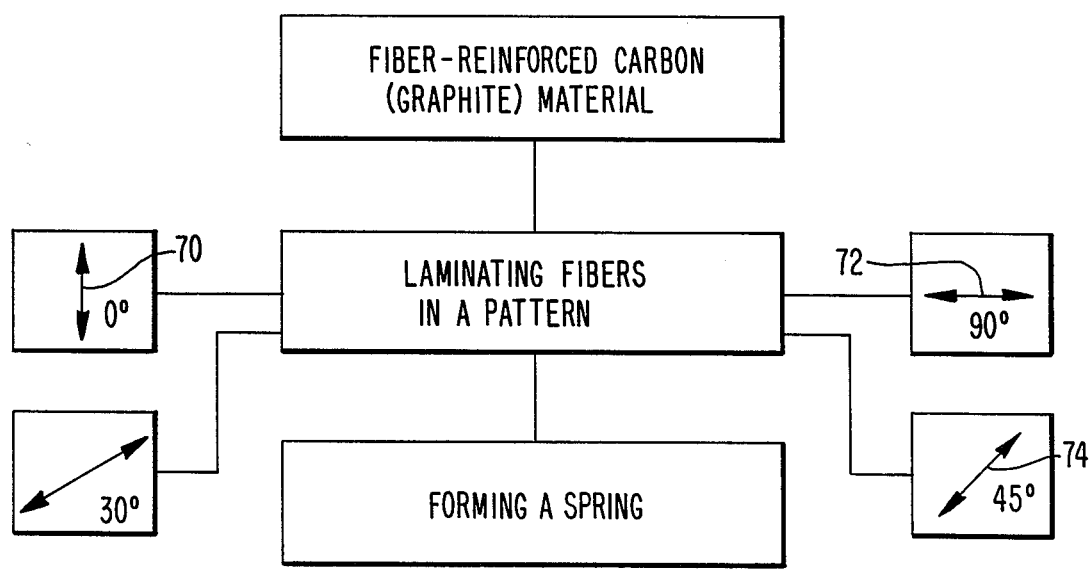
FIG. 7 is a block diagram showing steps in the manufacture of the deflection plates of a composite graphite, fiber-reinforced material.

The composite graphite flat spring is preferably produced with fibers running longitudinally and transversely, as shown diagrammatically in FIG. 7. When a percentage of transverse fibers are present, the composite has significant strength in the transverse direction. While this feature somewhat increases the weight of the composite flat spring 14, it remains significantly lighter. The weight of the graphite or carbon spring required to store energy in the foot 10 is approximately 80 grams of a total foot weight of 480 grams, while a steel spring to achieve the same affect would weigh approximately 580 grams of a 1080 gram foot. Since this is nearly twice the weight of any currently available prosthetic S.A.C.H. foot available, the weight is a crucial factor in the selection of the prosthetic feet to the user.

Preferably, the auxiliary deflection plate 20 is made from the same material. The spring structure 14, 20 is preferably surrounded with a protective sock 27, preferably made of a Kevlar brand material, about which the low-density flexible thermoplastic material 24 is molded.

As shown in FIG. 7, a certain number of transverse fibers are necessary to give the laminate strength and directions other than the longitudinal direction. By referring to the longitudinal direction as 0 degrees, as shown by the arrow 70, the composite is generally made by arranging fibers sequentially through multiple layers with the fibers oriented in the 90 and 45 degrees directions, shown by the arrows 72 and 74. Only a very few arrangements of fibers are needed to render the composite with sufficient strength without additional useless weight. Preferably, 40% of the fibers run in the 0 degree direction, while 40% run in the 30 degree direction, shown by arrow 65, and 20% run in the 90 degree direction.

The auxiliary composite deflection plate 20 has a first portion 60 extending in a relatively planar direction in contact with a corresponding portion of the primary deflection plate 14. The auxiliary composite deflection plate 20 preferably terminates an upwardly extending arcuate portion 62, located at about the natural area of transverse flexion of the foot. While the auxiliary plate is preferably made as a separate component of fiber-reinforced graphite or carbon as described, alternatively it may be made of a plastic material to provide auxiliary spring action. Or, it may be made integrally with the keel of the same or different material as the keel.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. An artificial foot comprising, in combination:
   a rigid keel portion comprising a rigid compression molded composite keel formed to define a cavity having a lower wall, a pair of upwardly-extending opposed side walls merging with said lower wall to define therebetween a cavity for receiving a lightweight material therein, and a top portion secured to the opposed side walls and extending therebetween, said top portion including means for securing the artificial foot to a prosthesis, said keel providing sufficient compressive and lateral strength for the user of said foot;
   spring means secured to a lower surface of said foot for providing energy absorption and release during flexion of the foot by the user; and
   a covering provided about said keel portion and spring means in the shape of a foot.

2. The artificial foot as defined in claim 1 wherein said keel is made from an aramid fiber-reinforced plastic material.

3. The artificial foot as set forth in claim 1 wherein the cavity of said keel is filled with a foam, plastic material.

4. The artificial foot as set forth in claim 1 wherein each of the side walls of said keel includes an upwardly-extending member, and said top portion is a cover plate which includes a corresponding recess for mating with said upwardly-extending members.

5. The artificial foot as set forth in claim 1 wherein the lower wall of said keel includes a first forwardly-extending portion, a second, intermediate, upwardly-extending portion for securing said spring means thereto, and a third rearwardly-extending portion extending aft of said spring means to define the heel portion of said foot.

6. The artificial foot as set forth in claim 5 wherein a medium density, flexible foam plastic material wedge is provided beneath said third portion of said keel.

7. The artificial foot as set forth in claim 1 wherein said spring means includes a primary deflection plate and an auxiliary deflection plate interposed between said primary deflection plate and said lower wall of said keel.

8. The artificial foot as set forth in claim 7 wherein said auxiliary deflection plate includes a forwardly-extending upwardly-oriented portion acting as a second spring during flexure of said foot.

9. The artificial foot as set forth in claim 7 wherein said primary deflection plate includes at least a pair of deflection plates secured to said keel and forwardly-extending therefrom in the toe portion of said keel, said plates being relatively slidable one with respect to the other.

10. The artificial foot as set forth in claim 7 wherein said primary deflection plate is made from a composite carbon-fiber material.

11. The artificial foot as set forth in claim 7 wherein each of said primary and said secondary deflection plates is made from a composite carbon-fiber material.

12. The artificial foot as set forth in claim 9 further including an abrasion-resistant material interposed about said primary and secondary deflection plates intermediate said deflection plates and said covering to inhibit abrasion of said covering therefrom.

13. The artificial foot as set forth in claim 1, wherein said keel is made from a plastic reinforced by aramid fibers.

14. An artificial foot comprising:
a rigid keel having means for securing said keel to a prosthesis of a user and including an opposed surface;
a spring means secured to said opposed surface of said rigid keel, said spring means comprising a principal deflection plate and an auxiliary deflection plate, said principal deflection plate storing and releasing energy during a normal walking mode and extending forwardly from said keel for a predetermined distance, said auxiliary deflection plate storing and releasing energy during an activity mode greater than a normal walking mode and extending forwardly from said keel for a distance less than said predetermined distance, and wherein a void is defined between a lower surface of a forward portion of said auxiliary deflection plate and an upper surface of said principal deflection plate.

15. The artificial foot as set forth in claim 14 wherein said keel is made from a rigid plastic material and said principal and said auxiliary deflection plates are made from a composite carbon fiber.

16. The artificial foot as set forth in claim 14 wherein said auxiliary deflection plate acts on a race for said principal deflection plate.

17. The artificial foot as set forth in claim 14 wherein said auxiliary deflection plate terminates in an upwardly extending arcuate portion located at about the natural area of transverse flexion of the foot.

18. The artificial foot as set forth in claim 17 wherein said auxiliary deflection plate includes a portion extending in a relatively planar direction in contact with a corresponding portion of the principal deflection plate.

19. The artificial foot as set forth in claim 14 wherein said principal deflection plate is made from a thermoset, carbon-reinforced material.

20. The artificial foot as set forth in claim 19 wherein said principal deflection plate is made from a plurality of thin, fiber-reinforced, carbon-composite, deflection plates which are slidable relative to one another.

21. The artificial foot as set forth in claim 14 wherein said principal deflection plate and said auxiliary deflection plate are made from a carbon-composite material.

22. An artificial foot comprising:
a rigid keel structurally adapted to be secured to a prosthesis of a user and having a lower surface defining a length extending generally in a fore and aft direction of the foot; and
spring means secured to said lower surface of the rigid keel at an intermediate region of said length of said lower surface and forwardly-extending therefrom for providing energy absorption and release during movement of the user, said spring means including a primary deflection plate made from a composite carbon-fiber material, wherein said spring means is surrounded by a sock immediately adjacent to said spring means.

23. The artificial foot as set forth in claim 22 wherein said primary deflection plate is a laminate of said composite carbon-fiber material.

24. The artificial foot as set forth in claim 22, wherein said keel is rigid.

25. The artificial foot as set forth in claim 22, wherein said lower surface of said keel is rigid.

26. The artificial foot as set forth in claim 24, wherein said keel is made of a plastic reinforced with aramid fibers.

27. The artificial foot as set forth in claim 22, wherein said spring means includes an auxiliary deflection plate interposed between said primary deflection plate and said keel.

28. The artificial foot as set forth in claim 22, wherein said keel and said spring means are surrounded by a low density foam plastic.

29. The artificial foot as set forth in claim 22, wherein a medium density foam plastic is positioned under a portion of said keel.

30. The artificial foot as set forth in claim 22, wherein said sock is made of aramid material.

31. The artificial foot as set forth in claim 22 wherein said composite carbon-fiber material has fibers oriented laterally and transversely for providing longitudinal and transverse strength to said spring means.

32. The artificial foot as set forth in claim 22 wherein said spring means further includes an auxiliary, composite laminate, deflection plate having an upwardly-extending portion located intermediate a length of said primary deflection plate at about the point of flexion of said foot to aid in energy absorption and release during flexion of said foot.

33. The artificial foot as set forth in claim 32 wherein said auxiliary composite deflection plate is made of a carbon-fiber laminate material.

* * * * *